(12) United States Patent
Forstner

(10) Patent No.: US 8,864,678 B2
(45) Date of Patent: Oct. 21, 2014

(54) BLOOD PRESSURE MEASURING METHOD AND BLOOD PRESSURE MANOMETER

(75) Inventor: Klaus Forstner, Asperg (DE)

(73) Assignee: Beurer GmbH & Co., Ulm (DE)

( * ) Notice: Subject to any disclaimer, the term of this patent is extended or adjusted under 35 U.S.C. 154(b) by 2041 days.

(21) Appl. No.: 10/572,997

(22) PCT Filed: Sep. 24, 2004

(86) PCT No.: PCT/EP2004/010725
§ 371 (c)(1),
(2), (4) Date: Apr. 3, 2007

(87) PCT Pub. No.: WO2005/030050
PCT Pub. Date: Apr. 7, 2005

(65) Prior Publication Data
US 2007/0232939 A1    Oct. 4, 2007

(30) Foreign Application Priority Data
Sep. 26, 2003   (DE) .................................. 103 44 803

(51) Int. Cl.
*A61B 5/02*    (2006.01)
*A61B 5/022*   (2006.01)

(52) U.S. Cl.
CPC ............. *A61B 5/02225* (2013.01); *A61B 5/022* (2013.01)
USPC ......................................... 600/495; 600/485

(58) Field of Classification Search
USPC .................. 600/481, 483–485, 495, 500, 501
See application file for complete search history.

(56) References Cited

U.S. PATENT DOCUMENTS

| 4,349,034 | A | * | 9/1982 | Ramsey, III | 600/494 |
| 4,543,962 | A | * | 10/1985 | Medero et al. | 600/495 |
| 4,592,365 | A | * | 6/1986 | Georgi | 600/493 |
| 5,099,853 | A | | 3/1992 | Uemura et al. | |
| 5,156,147 | A | * | 10/1992 | Warren et al. | 607/24 |
| 5,170,795 | A | | 12/1992 | Ramsey, III et al. | |
| 5,425,372 | A | * | 6/1995 | Takeda | 600/485 |
| 5,791,347 | A | * | 8/1998 | Flaherty et al. | 600/485 |
| 5,868,679 | A | | 2/1999 | Miyazaki | |
| 6,463,311 | B1 | * | 10/2002 | Diab | 600/324 |
| 6,554,773 | B1 | * | 4/2003 | Nissila et al. | 600/485 |
| 6,629,930 | B2 | * | 10/2003 | Palma et al. | 600/485 |

(Continued)

FOREIGN PATENT DOCUMENTS

| DE | 102 18 574 A1 | 11/2002 |
| EP | 0 850 592 A2 | 7/1998 |
| EP | 1 101 440 A1 | 5/2001 |
| EP | 1 258 223 A1 | 11/2002 |

OTHER PUBLICATIONS

De Meersman et al.: *Deriving respiration from pulse wave: a new signal-processing technique*, from *The American Physiological Society*, p. H1672-H1675, 1996.

Primary Examiner — Navin Natnithithadha
Assistant Examiner — Michael R Bloch
(74) Attorney, Agent, or Firm — Pauley Petersen & Erickson

(57) ABSTRACT

A blood pressure measuring method, according to which a pulse oscillogram of a patient is defined, the blood pressure is then determined from the pulse oscillogram and displayed. Reliable blood pressure values are obtained without additional cost to the user, by obtaining an evaluation criterion for the presence of haemodynamic stability from the individual pulse oscillogram, the determination of the blood pressure value or the determined blood pressure value being related to the criterion.

14 Claims, 3 Drawing Sheets

(56) References Cited

U.S. PATENT DOCUMENTS

| | | | |
|---|---|---|---|
| 6,827,687 B2* | 12/2004 | Narimatsu et al. | 600/485 |
| 2001/0049476 A1* | 12/2001 | Forstner | 600/494 |
| 2002/0058875 A1* | 5/2002 | Doten et al. | 600/484 |
| 2002/0082507 A1* | 6/2002 | Kolluri et al. | 600/485 |
| 2003/0092999 A1* | 5/2003 | Goto et al. | 600/485 |
| 2003/0097074 A1* | 5/2003 | Oka et al. | 600/490 |
| 2003/0167010 A1* | 9/2003 | Pinsky | 600/485 |
| 2003/0233048 A1* | 12/2003 | Silverman et al. | 600/500 |
| 2005/0004477 A1* | 1/2005 | Friedman et al. | 600/485 |

* cited by examiner

BLOOD PRESSURE MEASURING METHOD AND BLOOD PRESSURE MANOMETER

BACKGROUND OF THE INVENTION

1. Field of the Invention

This invention relates to a blood pressure measuring method, wherein a pulse oscillogram of a patient is determined and the blood pressure is thus detected and displayed, as well as to a sphygmomanometer for executing the method.

2. Discussion of Related Art

A non-invasively measuring blood pressure measuring method, or sphygmomanometer, is disclosed in European Patent Reference EP 1 101 440 A1. With this known method, or device, which is based on an oscillometrically-measuring, automatic method, one or several pulse oscillograms are selectively generated during a blood pressure measuring operation, in order to determine the blood pressure values from it or them, and to display them. In the first mode of operation, a systolic and a diastolic blood pressure value are determined in a manner known per se in one measurement cycle by a single pulse oscillogram. In the second mode of operation it is inter alia determined on the basis of several definite pulse oscillograms, between which a pause of 60 sec. is maintained, whether so-called hemodynamic stability exists. If there is no hemodynamic stability, this is indicated to the user by the output of an error code. Thus the user is informed when the measured blood pressure values have been adulterated because of insufficient hemodynamic stability, in particular insufficient circulatory rest wherein, however, the measuring time is not inconsiderably increased.

A method or device described by German Patent Reference DE 102 18 574 A1 for measuring blood pressure is also designed for detecting arrhythmia, wherein pulse wave information, such as the width, height and a time interval is detected for a plurality of beats. However, with a lack of circulatory rest, the blood pressure values per se cannot not be sufficiently accurately measured.

The lack of circulatory rest is considered to be the most important error influence during an outpatient measurement of arterial blood pressure. Patients doing their own measuring, but even medical specialists, do not possess criteria which are simple to detect during blood pressure measurements in order to judge circulatory rest. In many cases the length and size of a lack of circulatory rest is underestimated. Lack of circulatory rest has been documented in the course of measurements by physicians as the so-called "white-coat-effect", inter alia, and is known.

SUMMARY OF THE INVENTION

One object of this invention is to provide a blood pressure measuring method, or a sphygmomanometer, of the type mentioned above but in which a user, in particular a layman, can perform dependable blood pressure measurements with as little effort as possible.

This object is attained by characteristics described in this specification and in the claims.

In accordance with the method of this invention, while determining the individual pulse oscillogram an analysis regarding hemodynamic stability is also performed, wherein at least one hemodynamic parameter, and/or at least one other physiological parameter which correlates with the hemodynamic parameter, are evaluated with respect to chronological changes, and that assessment criteria for the presence of hemodynamic stability are obtained from the analysis, by which the determination of the blood pressure value or the determined blood pressure value are brought into correlation so that it can be ascertained whether the blood pressure value was obtained during hemodynamic stability, or if a corrected blood value is determined.

In connection with the sphygmomanometer, the arrangement evaluating also has an assessment arrangement embodied so that with it assessment criteria regarding the presence of hemodynamic stability are established during the determination of the individual pulse oscillogram. The display device has an indicator of hemodynamic instability.

Thus, a user can determine without additional cost outlay, without prolonging the measuring time, as well as without additional device adjustments, if a blood pressure measurement had been performed during hemodynamic instability. In this connection, the blood pressure values are displayed together with the indication of hemodynamic instability, so that for example specialists can also draw suitable conclusions. It is also possible that only the fact of an error effect is signaled, or that a repeat measurement is requested, or that such is automatically started.

User friendliness is enhanced if a warning indication is generated by the evaluation criteria if they deviate from preset or predeterminable threshold criteria, wherein the type of the deviation can also be preset.

An assessment of hemodynamic stability directly linked to the blood pressure measurement is achieved in such a way that the individual pulse oscillogram is subjected to an analysis regarding hemodynamic stability.

The fact that, prior to obtaining the assessment criteria, influential values of artifacts and/or arrhythmia are suppressed, contributes to the increase of the accuracy of the assessment criteria.

In detail, various steps for deriving the assessment criteria include a time-dependent pulse period progression, and/or a pulse amplitude progression, and/or the pulse shape, and are determined and analyzed from the pulse oscillogram. The assessment criteria from the pulse period progression, the pulse amplitude progression, the pulse shape, or from a combined evaluation are formed from at least two items of this base information, wherein particularly dependable assessment criteria are obtained if the basic information in an at least partial combination is included in the evaluation.

In this case, advantageous embodiments include comparing pulse period lengths of at least a starting range and an end range of the pulse oscillogram to each other. A deviation of the pulse period lengths of the starting range and the end range becomes the basis for the assessment criteria, or the trend change of the pulse period progression is determined.

A value which is suitable for comparison with threshold value criteria includes the deviation of the lengths of the pulse period calculated by the pulse oscillogram as the difference of the lengths of the periods of the starting range and the end range, as a function of a mean pulse period length of the pulse oscillogram.

Other measures for assessing the hemodynamic stability include determining the entire progression of all pulse periods in regard to their chronological change, which is used as a measure for the hemodynamic stability, or the entire progression of the pulse-specific systolic times in regard to their changes over time is determined, and this change is used as a measure of the hemodynamic stability.

The dependability of the assessment criteria is improved if an assessment of the constancy of the entire chronological pulse period progression in particular is included when forming the assessment criteria.

Advantageous measures for using the pulse amplitude progression for forming the assessment criteria include a rise in the ascending branch of the envelope or a rise in its descending branch, or a plateau width around their maximum, or a combination of at least two of these characteristic values from the pulse amplitude progression, used as characteristic values for forming the assessment criteria.

The shape of the pulse or curve can be evaluated so that the analysis of the pulse shape includes a determination of one or several rises at least at one point of an ascending and/or a descending pulse flank. A chronological change in each rise at the respective points or a ratio of the rises at least at two points of a pulse is checked for different pulses as assessment criteria for the hemodynamic stability.

In this or a similar manner, it is also possible to determine the change of the systolic time as assessment criteria for hemodynamic stability. It is possible here, for example, to make a meaningful base value in each the base area of a pulse and the top area of a pulse the basis for determining the length of the systole. This time is correlated with the ventricular contraction time of the heart.

If, for example, different meaningful characteristic values result from the pulse period progression and the pulse amplitude progression, then the dependability for determining the hemodynamic stability can be increased if the pulse period progression, the pulse amplitude progression and/or the pulse shape are weighted identically or differently, depending on their markedness, for forming the assessment criteria.

Alternatively or additionally, an option for assessing the hemodynamic stability includes, for assessing the hemodynamic stability, a breathing frequency signal, an electrocardiogram signal and/or a skin impedance measurement signal that are determined as other, or added parameters, and evaluated in regard to a chronological change during the individual blood pressure measurement. Thus, for example, the breathing frequency signal is obtained from the analysis of the pulse oscillogram, or by an additional sensor arrangement.

Another embodiment of the sphygmomanometer includes the assessment arrangement designed for detecting a pulse period progression, and/or a pulse amplitude progression, and/or pulse forms from the pulse oscillogram, and the formation of the assessment criteria from the pulse period progression, and/or the pulse amplitude progression, and/or a pulse form change.

In an alternative or additional design option, the assessment arrangement is designed for detecting at least one physiological additive factor correlated with a change of the hemodynamics which relates to, for example, a breathing frequency signal, an electrocardiogram signal and/or a skin impedance signal.

The mentioned measures can be provided, for example, in a sphygmomanometer at the upper arm or the wrist, wherein as a rule the evaluation and display device is arranged in a housing on the cuff, but can also be arranged removed or removable from the cuff. For example, the blood pressure values can be displayed together with the date and time and/or the pulse frequency and stored in a suitable memory. Preset or predeterminable threshold values can be displayed, stored and monitored. Also, an interface for reading out detected data and/or reading in preset values or configurations of the evaluating device can be provided on the device.

BRIEF DESCRIPTION OF THE DRAWINGS

This invention is explained in greater detail in view of exemplary embodiments in the drawings, wherein.

DESCRIPTION OF PREFERRED EMBODIMENTS

Figure 1:
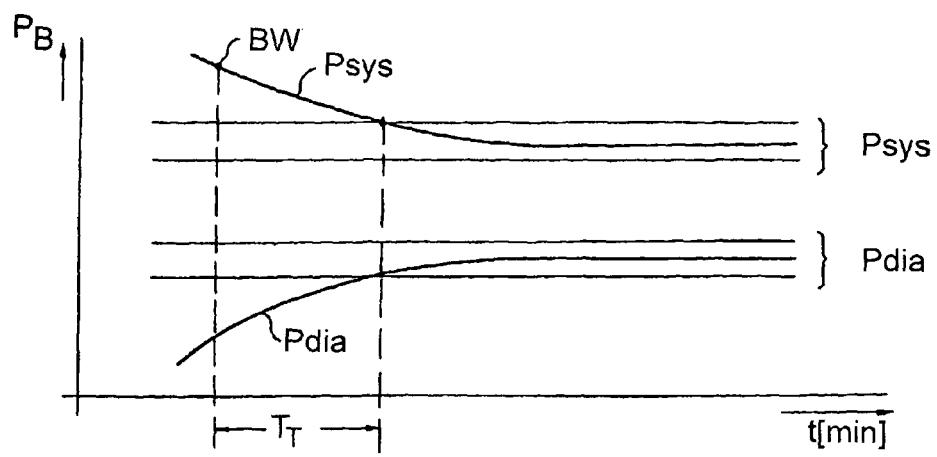
FIG. 1 shows typical transitions of a systolic blood pressure progression and a diastolic blood pressure progression from areas of hemodynamic instability to stationary areas in a graphical representation.

In a diagram, in which the blood pressure $P_B$ has been applied over the time t, FIG. 1 represents transition times $T_T$ of a systolic blood pressure progression $p_{sys}$ and of a diastolic blood pressure progression $P_{dia}$ from a stress value BW into a respective stationary range $\Delta p_{sys}$ or $\Delta p_{dia}$ or $\Delta P_{dia}$. The values $\Delta p_{sys}$ and $\Delta p_{dia}$ are derived from the physiological beat volume variation, as well as short-term vascular width changes in their effects on the blood pressure.

Circulatory rest exists if the systolic and diastolic blood pressure $\Delta_{sys}$ or $\Delta p_{dia}$, as well as the heart frequency, of a patient move around respectively valid stationary values, i.e. not towards a resting value or away from a resting value. Circulatory rest is a prerequisite for the validity of internationally recognized threshold values of arterial blood pressure (WHO, 1999, as well as JNC7, 2003). These threshold values are used as target values when adjusting arterial blood pressure.

Systolic and diastolic blood pressure values change their values with the beat. This is the physiological short term variation of the arterial blood pressure. Typically, it can amount systolically to up to 12 mmHg, and diastolically up to 8 mmHg. Besides these beat-related changes, however, the blood pressure of the resting, relaxed human is quasi stationary, i.e. changeable only very slowly.

Circulatory rest no longer exists if humans undergo a physical load or undergo physical stress. In these cases, the systolic blood pressure rises as a rule, the diastolic blood pressure drops slightly as a rule, but can also rise, and the pulse frequency rises regularly. Any organism adjusts in this way with a higher heartbeat volume to the stress situation which has arisen.

Following a physical or psychic psychological stress, the organism requires a transition time $T_T$ until circulatory rest again prevails. The transition time $T_T$ depends on a number of factors, in particular extent and type of the stress, age, sex, training state, and/or previous illness.

As a rule, it is not possible to estimate the effects on the time of rest of the sum of the factors mentioned. For the layman, in particular, it is difficult to obtain information regarding the lack of circulatory rest. In many cases, the transition time $T_T$ is considerably underestimated in actuality, so that many blood pressure measurements do not yet take place during circulatory rest.

Figure 2:
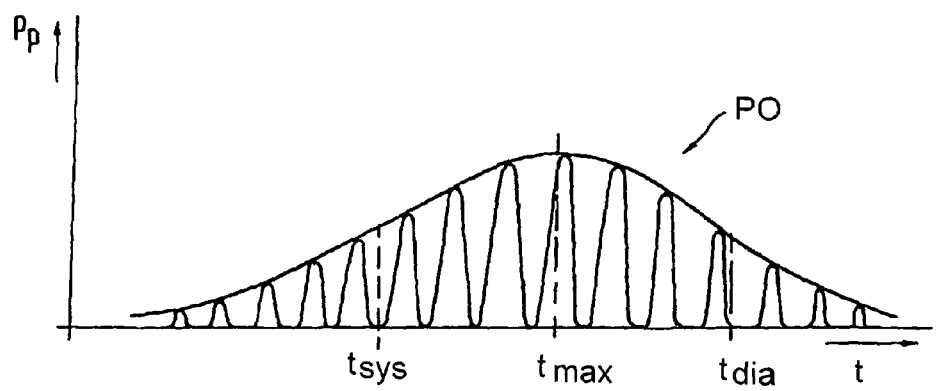
FIG. 2 shows a graphical representation of a pulse oscillogram with an envelope.

Typical times until relative circulatory rest has been achieved (±10% of values at rest) are 2 min to 5 min. With older people and patients with previous illnesses, values of up to 15 min can occur. But the circulatory rest represents the most important error factor in the determination of the blood pressure at rest of a patient and is therefore automatically diagnosed by the measures described in greater detail in each individual blood pressure measurement cycle, where hemodynamic stability diagnosis=HSD. This is based on a pulse oscillogram PO, such as represented in FIG. 2 by way of example. Such a pulse oscillogram PO is always prepared in a known manner during the measurement in connection with the method of oscillometric measurement applied here.

During a cycle of the oscillometric blood pressure measurement by the present hemodynamic stability diagnosis, a check is made whether or not the respective patient is in hemodynamic rest. The check for hemodynamic stability leads to a result indication which is preferably associated with the target values of systolic blood pressure value, diastolic blood pressure value and pulse frequency. During this the hemodynamic stability is quantitatively determined, however, a binary indication, whether or not the stability is considered to be sufficient, is provided to the end user.

For determining the hemodynamic stability, the user strives not to perform any activities or device settings during or after the measurements. The measuring time of the blood pressure measurement is not prolonged by the hemodynamic stability diagnosis, because the diagnosis takes place in the same measuring cycle, and the subsequent signal analysis leads practically without delays to an indication of the final results.

The determination of the hemodynamic stability provides the result of the oscillometric blood pressure measurement, with the additional information, as to whether the required measurement conditions for determining the resting blood pressure had been met. If the rest requirements have not been met, the hemodynamic diagnosis identifies the obtained measurements with a suitable indication as "measurements while circulatory rest is lacking".

With a pulse oscillogram, such as is represented by example in FIG. 2 and which represents the progression of the pulse pressure $p_p$ over the time t, the amplitude of the individual pulses during the release of the cuff pressure increases to a maximum, which on the basis of physical laws is achieved when the cuff pressure corresponds to the mean arterial blood pressure (MAP). Subsequently, the amplitude of the individual pulses decreases again. The amplitude progression is shown by the envelope.

The systolic blood pressure therefore is reached in the rising portion of the envelope, for example at a time $t_{sys}$, and the diastolic blood pressure in the falling portion of the envelope, for example at a time $t_{dia}$. These times result from calibration constants preset in the devices and are derived from the pulse oscillogram. This applies to the systole and the diastole. However, even before the cuff releases the compressed artery again, the pressure pulses occurring on the heart side of the cuff have an effect on the cuff pressure, beat pulses, so that oscillation of the cuff pressure, and thus also of the pulse oscillogram, becomes noticeable before the systolic blood pressure $p_{sys}$ is reached while lowering the cuff pressure. This effect can also be used in the diagnosis of the hemodynamic stability.

Figure 3:
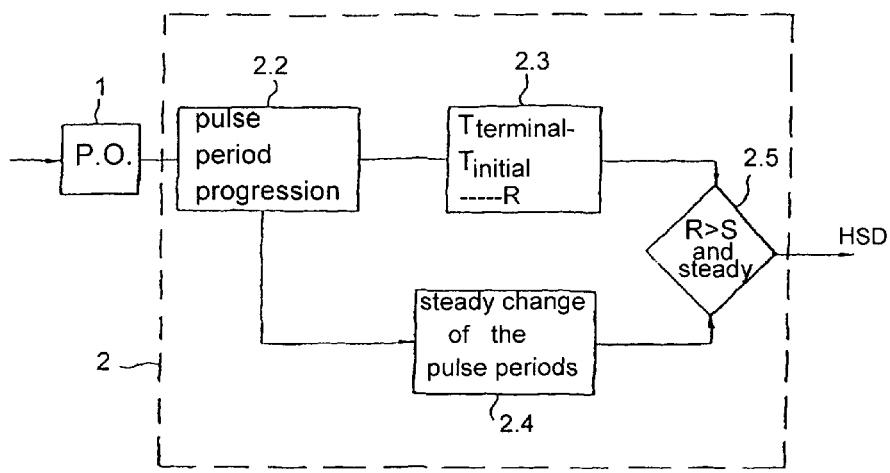
FIG. 3 shows a schematic representation for deriving assessment criteria for the hemodynamic stability from a pulse oscillogram.

For diagnosing the hemodynamic stability, in accordance with FIG. 3 and based on the pulse oscillogram obtained in a measuring stage 1, during a pulse period sequence analysis period 2 the pulse period progression is determined in an evaluation stage 2.2, and from this the pulse sequence in a determination stage 2.3, and the constancy of the change of the pulse periods while measuring in a detection stage 2.4. During this, in the determination stage 2.3 the chronological pulse distance is advantageously measured in a starting time period $T_{initial}$, which lies before reaching the maximum $T_{max}$, and in a later time period $T_{terminal}$, and the difference of the pulse distances $T_{terminal}-T_{initial}$ is divided by a standardization value, for example the mean pulse distance $T_{mittel}$, in order to arrive at an assessment value R, which is compared with a preset or predeterminable threshold S in a decision stage 2.5. In this case, the arithmetic mean value of all detected pulse distances of the pulse oscillogram PO, for example, can be made the basis of the mean pulse distance $T_{mittel}$.

Furthermore, a constancy evaluation is supplied to the decision stage 2.5 parallel with the assessment criteria R in the form of a pulse period change, which is performed in the detection stage 2.4. Then, in the decision stage 2.5 it is determined on the basis of preset or predeterminable criteria whether or not hemodynamic stability exists during the blood pressure measurement. It is already possible with this pulse period sequence analysis to form conclusions regarding the presence of hemodynamic stability, or the presence of stationary conditions, and a corresponding indication for the display can be generated. In order to obtain as large as possible a time difference for detecting the initial and later pulse distances $T_{initial}$ and $T_{terminal}$, and therefore an improved selectivity, it is advantageous to include the initial pulse distances $T_{initial}$ as early as possible, i.e. to include the pulse obtained prior to reaching the systolic pressure $p_{sys}$ if possible, as mentioned above. The later pulse distance $T_{terminal}$ should be detected during a later time period of the descending pulse oscillogram range which has a relation to the time of the diastolic pressure determination, if possible.

An analysis of the chronological progression of the pulse periods can be applied to all pulses within a measurement because their chronological change is detected by a suitable statistical analysis, for example a progression analysis.

Figure 4A:
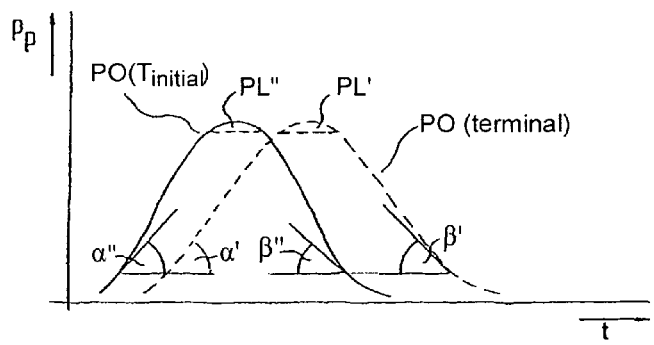
FIGS. 4A and 4B show envelopes of different pulse oscillograms with characteristic values, each in a schematic representation.
Figure 4B:
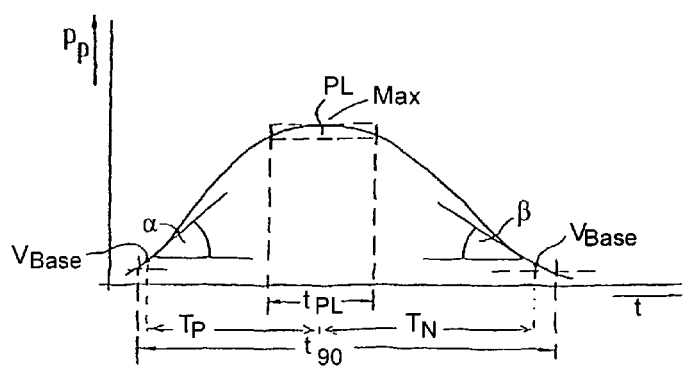

A further statement regarding the presence of hemodynamic stability can be obtained by the evaluation of the pulse amplitudes, which are marked by the envelope of the pulse oscillogram PO and represented for different cases in FIGS. 4A and 4B. A theoretical envelope of a pulse oscillogram PO in an initial time period $T_{initial}$ is represented by way of example in FIG. 4A by a solid line. A dashed line shows the progression of the envelope at a later time period $T_{terminal}$. The different envelopes are part of statistical circulation conditions and show as characteristic values, for example, an ascending angle α", α' and a descending angle β", β', and/or relative plateau areas PL', PL".

An envelope resulting from measuring technology is represented in FIG. 4B, which is created as a cumulative curve because of the superimposition over the measuring time. It is possible to also derive appropriate characteristic values (α, β, PL) from the cumulative curve, which are a substantial function of hemodynamic stability. For example, it is possible to define the plateau length $t_{PL}$ as a period of time in which the pulse pressure $p_p$ lies no less than a preset percentile value (for example 10%) below the maximum. For obtaining a suitable statement, the plateau length can be related to a further length of time during which the pulse pressure $p_p$ does not lie less than a low preset percentile value, for example 90%, below the maximum, for example $t_{90}$, so that $R_{PL}=T_{PL}/T_{90}$ results as the characteristic value, for example.

Also, the ascent time and the descent time can be determined by a value $V_{Base}$ related to the maximum for both flanks of the pulse oscillogram. The descent time $T_N$ and the ascent time $T_p$ result in this way. The two values can be placed in relation to each other, for example by a steepness index $S=T_N/T_p$. The steepness index S changes during hemodynamic instability.

The characteristic values in accordance with FIGS. 4A and 4B can be used for characterizing the pulse amplitude progression and for thus drawing conclusions regarding the presence of hemodynamic stability.

Figure 4C:
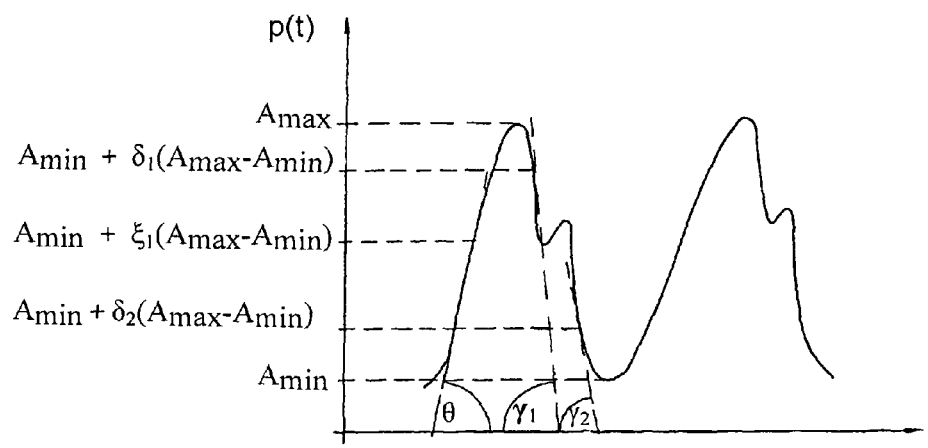
FIG. 4C shows a graphical representation of a pulse curve progression.

Further assessment criteria for hemodynamic stability result from a pulse or curve shape analysis by distinguishing characteristics which show, for example in accordance with FIG. 4C, a pulse curve progression p(t) over the time t. During this the changes of steepness of ascending and/or descending pulse flanks during the measurement are for example determined. In the ascending pulse flank the rise is determined for a point $\xi$ ($A_{max}-A_{min}$)+$A_{min}$), wherein $A_{max}$ is the maximum and $A_{min}$ the minimum of the respective amplitude, and $\xi$ represents a value between zero and one, and the rise is expressed by the angle theta. In the descending pulse flank the rises for the points $\delta_1$ ($A_{max}-A_{min}$)+$A_{min}$, as well as $\delta_2$ ($A_{max}-A_{min}$)+$A_{min}$ are calculated, wherein $\delta_1$ and $\delta_2$ are also values between zero and one and the rises are expressed by the angles $\gamma_1$ and $\gamma_2$. Now hemodynamic changes can be detected by chronological changes of the rises theta, $\gamma_1$ and $\gamma_2$, so that the drawing of conclusions regarding the hemodynamic stability is possible. In particular, the relationships of $\gamma_1/\theta$, as well as $\gamma_2/\theta$, are of diagnostic interest.

A change in the systole length can also be determined in a corresponding or similar manner, for example between a characteristic base value and a peak value defined in the area of the maximum. However, the entire progress of the pulse-specific systole time can be subjected to an analysis, for example a statistical trend analysis. The systole length can be used for assessment criteria.

Figure 5:
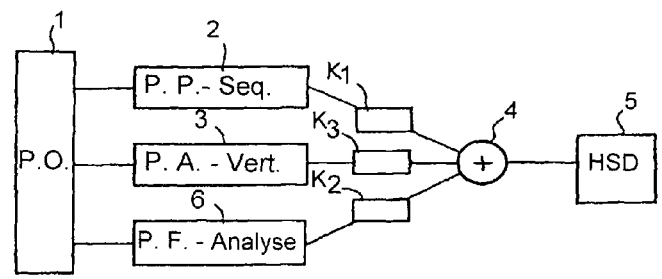
FIG. 5 shows a schematic representation for a derivation of an assessment of the hemodynamic stability.

In order to obtain the highest possible dependability for the formation of assessment criteria, regardless of whether hemodynamic stability exists during the blood pressure measurement, at least two of the evaluations, the pulse period sequence analysis in accordance with FIG. 3, the pulse amplitude analysis and the pulse shape analysis in combination with each other, can be observed together, as schematically represented in FIG. 5.

In accordance with FIG. 5, starting with the pulse oscillogram PO obtained in the measuring stage 1, the pulse period sequence analysis 2, the pulse amplitude progression analysis 3 and the pulse shape analysis 6 are performed in parallel, and results are calculated together in a linkage stage 4, in order to form assessment criteria in an assessment stage 5 whether or not hemodynamic stability prevails. Depending on the characteristic markedness of the pulse period sequence analysis 2, the pulse amplitude progression analysis 3 and/or the pulse shape analysis 6, different weightings kappa, kappa$_2$, kappa$_3$ of these analyses can be performed prior to or during the linkage stage 4 or in the assessment stage 5 for forming the assessment criteria wherein, for example, also a combination of only two of these analyses, or the values of the statements obtained from them, can be linked with each other. The result as to whether or not hemodynamic stability exists is then used for the optical and/or acoustic display, or the automatic performance of a repeat measurement wherein, in case of non-existent hemodynamic stability, an appropriate warning display or indication of the blood pressure values takes place. An embodiment of the blood pressure measuring method or the device can be realized in which the result of the hemodynamic stability analysis is used for correcting the blood pressure values.

Preferably, the mentioned method steps or process stages for assessing the hemodynamic stability are realized by software through suitable programs in a micro-controller of an evaluating device of the sphygmomanometer. Here, the analysis of the pulse oscillogram for assessing the hemodynamic stability can be performed within a time frame and/or frequency range (spectral analysis). To the extent it is useful, it is possible to provide suitable peripheral components for also controlling the display correspondingly, if desired for storing suitable values, or also for controlling an interface for input/output.

A selection of parameter sets can also be provided in the evaluating device, for example for automatically recognizing the patient cuffs, or to take other data into consideration. It is then possible on the basis of the parameter sets to select individually matched programs in order to perform an appropriately refined diagnosis of the hemodynamic stability.

Based on characteristic properties of the pulse period progression and/or the pulse amplitude progression, it is also possible to detect influential values other than the hemodynamic instability as the effective causes of erroneous measured values.

In a further embodiment, during the measurement as to whether or not hemodynamic stability exists, alternatively or additionally to the above described analysis of the individual pulse oscillogram PO, one or several physiologically additive or further parameters are detected, which correlate with a chronological change of the hemodynamics. Such secondary parameters are, for example, the breathing modulation or breathing frequency, an electrocardiogram signal, or a skin impedance signal, which changes because of varying the stretching during breathing, or the moisture conditions. In this case, the breathing modulation can be detected, for example, while analyzing the pulse oscillogram PO prepared during the blood pressure measurement, or by an additional sensor device. Electrodes can be arranged on the cuff of the sphygmomanometer for obtaining the electrocardiogram signal, while a counter-electrode is separately provided. With a connection to the sphygmomanometer, in particular to its evaluating device, it is possible to obtain the secondary parameters by a justifiable cost outlay while obtaining the assessment criteria of the hemodynamic stability. In a similar manner, it is possible to determine the absolute pulse speed and to take it into consideration, for example, by a separate pulse sensor.

The invention claimed is:

1. A blood pressure measuring method, comprising:
   determining a blood pressure value of a patient during a single blood pressure measurement cycle;
   measuring a pulse sequence of the patient during the single blood pressure measurement cycle;
   automatically determining with an evaluating device whether the blood pressure value was measured at a circulatory rest of the patient during the single blood pressure measurement cycle, by at least one of:
   a) ascertaining a pulse period progression (2.2) of the pulse sequence, comparing pulse period durations of at least one initial range and one terminal range of the pulse period progression and using any deviation in the pulse period durations of the initial range ($T_{initial}$) and of the terminal range ($T_{terminal}$) as an assessment criterion for determining the circulatory rest, or the entire progression of all the pulse periods of the pulse sequence is ascertained with regard to a change over time, and the change is used as a measure of the circulatory rest; or
   b) ascertaining a pulse amplitude progression (3) of the pulse sequence, and from the pulse amplitude progression determining a gradient (a) in an ascending range thereof, a gradient (β) in a descending range thereof, a plateau width (PL) about a maximum thereof, or a combination thereof; or c) ascertaining a pulse curve of the pulse sequence, analyzing a shape of the pulse curve (6) to determine one or more gradients at at least one point in an ascending or descending pulse edge, and examining a change in the pulse curve over time in the one or more gradients, or a ratio of the gradients at at least two points for various pulses; and the evaluating device determining and indicating whether the blood pressure value was obtained during the circulatory rest, or whether a corrected blood pressure value is to be determined;

wherein the evaluating device automatically performs at least two of: step a), step b), or step c), to determine the circulatory rest, and further comprising applying a different weighting to each of the at least two of the steps a), b), or c) in determining the circulatory rest.

2. The method in accordance with claim 1, wherein the evaluating device automatically performs each of step a), step b), and step c) to determine the circulatory rest.

3. The method in accordance with claim 2, further comprising applying a different weighting to each of the steps a), b), or c) in determining the circulatory rest.

4. The method in accordance with claim 1, wherein a warning indication is generated or a repeat blood pressure measurement cycle is initiated if the evaluating device does not determine that the single blood pressure measurement cycle was measured at the circulatory rest of the patient.

5. The method in accordance with claim 1, wherein the single blood pressure measurement cycle is determined by a sphygmomanometer.

6. The method in accordance with claim 1, further comprising suppressing influential values of at least one of artifacts or arrhythmia.

7. The method in accordance with claim 1, wherein the deviation in the pulse period durations is calculated as a difference between the period durations of the initial range and the terminal range.

8. The method in accordance with claim 1, wherein the entire progression of all pulse periods in regard to the change over time is determined and used as a measure for the circulatory rest.

9. The method in accordance with claim 1, further comprising assessing a constancy of the pulse period progression in the forming of the assessment criterion.

10. The method in accordance with claim 1, further comprising determining and evaluating at least one of a breathing frequency signal, an electrocardiogram signal, or a skin impedance measurement signal in regard to a chronological change during the single blood pressure measurement cycle.

11. The method in accordance with claim 10, wherein the breathing frequency signal is obtained from at least one of an analysis of the pulse sequence or by an additional sensor arrangement.

12. The method in accordance with claim 1, wherein a diagnosis of the circulatory rest is an automated correction of error effects.

13. The method in accordance with claim 1, wherein the determination of the blood pressure value is performed by a sphygmomanometer comprising an inflatable cuff, and the evaluating device is arranged thereon or connected to the sphygmomanometer, and at least one of the sphygmomanometer or the evaluating device includes a unit measuring the pulse sequence and a display device, the display device including an indicator of the circulatory rest.

14. The method in accordance with claim 1, wherein the single blood pressure measurement cycle is determined in a single cuff pressure increase and release cycle.

* * * * *